(12) United States Patent
Huang et al.

(10) Patent No.: US 11,872,083 B2
(45) Date of Patent: Jan. 16, 2024

(54) ULTRASONIC PROBE HOLDER WITH ABUTMENT PROTRUSIONS AND VIBRATOR FOR ULTRASONIC DEVICE AND METHOD FOR MEASURING ELASTICITY OF TISSUE

(71) Applicant: NATIONAL CHENG KUNG UNIVERSITY, Tainan (TW)

(72) Inventors: Chih-Chung Huang, Tainan (TW); Pei-Yu Chen, New Taipei (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 230 days.

(21) Appl. No.: 17/545,428

(22) Filed: Dec. 8, 2021

(65) Prior Publication Data
US 2023/0124311 A1    Apr. 20, 2023

(30) Foreign Application Priority Data
Oct. 20, 2021 (TW) ................................ 110138909

(51) Int. Cl.
*A61B 8/08* (2006.01)
*A61B 8/00* (2006.01)

(52) U.S. Cl.
CPC ............ *A61B 8/485* (2013.01); *A61B 8/4209* (2013.01); *A61B 8/4433* (2013.01); *A61B 8/4444* (2013.01); *A61B 8/5207* (2013.01); *A61B 8/42* (2013.01); *A61B 8/4254* (2013.01)

(58) Field of Classification Search
CPC ..... A61B 8/485; A61B 8/4444; A61B 8/5207; A61B 8/085; A61B 8/5223; A61B 8/4433; A61B 8/42; A61B 8/4209; A61B 8/4254
See application file for complete search history.

(56) References Cited

U.S. PATENT DOCUMENTS

| | | | | |
|---|---|---|---|---|
| 5,094,243 | A * | 3/1992 | Puy ...................... | G10K 11/004 600/459 |
| 2014/0094701 | A1* | 4/2014 | Kwartowitz ......... | A61B 8/5223 600/438 |
| 2017/0164929 | A1* | 6/2017 | Kwartowitz ......... | A61B 8/5223 |
| 2018/0263597 | A1* | 9/2018 | Tchang ................ | G10K 11/355 |
| 2021/0018606 | A1* | 1/2021 | McCaw ................ | G01N 29/34 |
| 2021/0267572 | A1* | 9/2021 | Sutton .................. | A61B 8/4209 |

FOREIGN PATENT DOCUMENTS

| | | | | |
|---|---|---|---|---|
| EP | 2961323 A4 * | 2/2017 | .......... | A61B 8/4209 |
| WO | WO-2012078280 A1 * | 6/2012 | .......... | A61B 5/0048 |
| WO | WO-2020181394 A1 * | 9/2020 | .......... | A61B 8/4209 |

* cited by examiner

*Primary Examiner* — Serkan Akar
*Assistant Examiner* — James F McDonald
(74) *Attorney, Agent, or Firm* — Muncy, Geissler, Olds & Lowe, P.C.

(57) ABSTRACT

An ultrasonic device is provided for use on a biological tissue, and includes a base assembly on which a vibrator is mounted, and an ultrasonic probe. The base assembly includes an annular base having at least two pairs of abutment protrusions for abutting against the biological tissue, and an installation base coaxially disposed on and rotatable relative to the annular base between two test positions. The installation base has a through hold in which the ultrasonic probe is inserted.

8 Claims, 6 Drawing Sheets

ULTRASONIC PROBE HOLDER WITH ABUTMENT PROTRUSIONS AND VIBRATOR FOR ULTRASONIC DEVICE AND METHOD FOR MEASURING ELASTICITY OF TISSUE

CROSS-REFERENCE TO RELATED APPLICATION

This application claims priority of Taiwanese Invention Patent Application No. 110138909, filed on Oct. 20, 2021.

FIELD

The disclosure relates to a device and a method for measuring a biological tissue, and more particularly to a device and a method for measuring elasticity of a biological tissue.

BACKGROUND

Conventional ultrasonic measurement systems for measuring elasticity of a biological tissue usually include a vibrator and an ultrasonic probe that are combined together. In use, the vibrator and the ultrasonic probe simultaneously abut against a surface of the biological tissue (e.g., a body surface of a test subject), and then the vibrator is driven to apply a mechanical wave to a part of the biological tissue against which the combined vibrator and ultrasonic probe abut, and at the same time the ultrasonic probe performs ultrasonic sensing on the part of the biological tissue. Then, elasticity data of the part of the biological tissue can be obtained through analysis of ultrasound images.

The ultrasonic probe is usually configured to emit an ultrasonic signal that travels as a fan-shaped arcing beam in a longitudinal direction (i.e., traveling direction of the ultrasonic signal), so as to measure tissue elasticity of a longitudinal section of the biological tissue. Thus, when an operator uses a conventional ultrasonic measurement system to sequentially measure tissue elasticity of different sections from a single site of the biological tissue (these sections are termed "longitudinal sections" herein because they are defined by the traveling direction (longitudinal direction) of the ultrasonic signal emitted by the ultrasonic probe), the combined vibrator and ultrasonic probe, while being held to abut against the site, has to be rotated to change orientation of the fan-shaped arcing beam. Such an operation is likely to cause a position of the combined vibrator and ultrasonic probe to shift relative to the site, which will induce a shift between center parts of the two longitudinal sections.

In addition, conventional ultrasonic measurement systems can only be used to measure the longitudinal elasticity of the biological tissue, and cannot be used to measure elasticity of the biological tissue in lateral directions because of its inability to generate shear waves that travel in the lateral directions.

SUMMARY

Therefore, an object of the disclosure is to provide an ultrasonic device that can alleviate at least one of the drawbacks of the prior art.

According to the disclosure, the ultrasonic device includes a base assembly, a vibrator and an ultrasonic probe. The base assembly includes an annular base and an installation base. The annular base surrounds an Z-axis, and has an annular surface disposed to face the biological tissue and surrounding the Z-axis, and at least two pairs of abutment protrusions that protrude from the annular surface for abutting against the biological tissue. For each pair of the abutment protrusions, the abutment protrusions are disposed symmetrically with respect to the Z-axis. The installation base is coaxially disposed on the annular base and is operable to rotate relative to the annular base about the Z-axis between at least two testing positions that respectively correspond to the at least two pairs of the abutment protrusions. The installation base is formed with an installation through hole that extends along the Z-axis. The vibrator is mounted to the base assembly, and is operable to vibrate for applying a mechanical wave to the biological tissue through the abutment protrusions. The mechanical wave has a frequency in a range of from 100 Hz to 400 Hz. The ultrasonic probe is inserted into the installation through hole along the Z-axis for abutting against the biological tissue to perform ultrasonic testing on the biological tissue. When the installation base is positioned in any one of the at least two testing positions, the ultrasonic probe that is inserted in the installation through hole is operable to produce an ultrasonic signal travelling as a fan-shaped arcing beam, of which a chord direction is parallel to a virtual line that interconnects the corresponding one of the at least two pairs of the abutment protrusions.

Another object of the disclosure is to provide a method for measuring elasticity of the biological tissue. The method can alleviate at least one of the drawbacks of the prior art.

According to the disclosure, the method includes: (A) a first scanning step of using the ultrasonic device of Claim 1 to perform, when the installation base is positioned in one of the at least two testing positions, image scanning on the biological tissue when the vibrator does not vibrate to obtain a reference ultrasound image, wherein the ultrasonic signal induces an ultrasonic shear wave that travels in the biological issue; (B) a second scanning step of using the ultrasonic probe to perform, when the installation base is positioned in said one of the at least two testing positions and the vibrator is vibrating to apply a mechanical wave to the biological tissue, image scanning on the biological tissue with a predetermined scanning frequency, so as to obtain a plurality of testing ultrasound images; (C) a displacement analysis step of calculating, for each of the testing ultrasound images, a timewise displacement of the ultrasonic shear wave relative to the reference ultrasound image at a time point the testing ultrasound image was taken, so as to convert the testing ultrasound image into a respective displacement image; (D) a spatial-frequency-domain (SFD) transforming step of transforming the displacement images that correspond to the testing ultrasound images into a spatial frequency domain, so as to obtain a plurality of SFD displacement images that respectively correspond to the displacement images; (E) a first filtering step of performing, for each of the SFD displacement images, filtering on the SFD displacement image with respect to a longitudinal direction in which the ultrasonic signal travels to obtain a longitudinal SFD displacement image, the longitudinal direction being parallel to the Z-axis; (F) a second filtering step of performing, for each of the SFD displacement images, filtering on the SFD displacement image with respect to lateral directions that are perpendicular to the longitudinal direction to obtain a set of lateral SFD displacement images that respectively correspond to the lateral directions; (G) a first time-domain transforming step of transforming the longitudinal SFD displacement images that are obtained respectively from the SFD displacement images into a time domain, so as to obtain a plurality of longitudinal time-domain displacement images; (H) a second time-domain transforming step of transforming the sets of the lateral SFD displacement images that are obtained respectively from the SFD displacement images into the time domain, so as to obtain a plurality of sets of lateral time-domain displacement images, wherein the lateral time-domain displacement images in each of the sets respectively correspond to the lateral directions; and (I) an elasticity analysis step of calculating longitudinal elasticity of the biological tissue based on a timewise variation of phases of the longitudinal time-domain displacement images, and calculating lateral elasticities of the biological tissue based on timewise variations of phases of the lateral time-domain displacement images. The longitudinal elasticity and the lateral elasticities of the biological tissue are usable for making medical determinations related to muscles or tendons.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
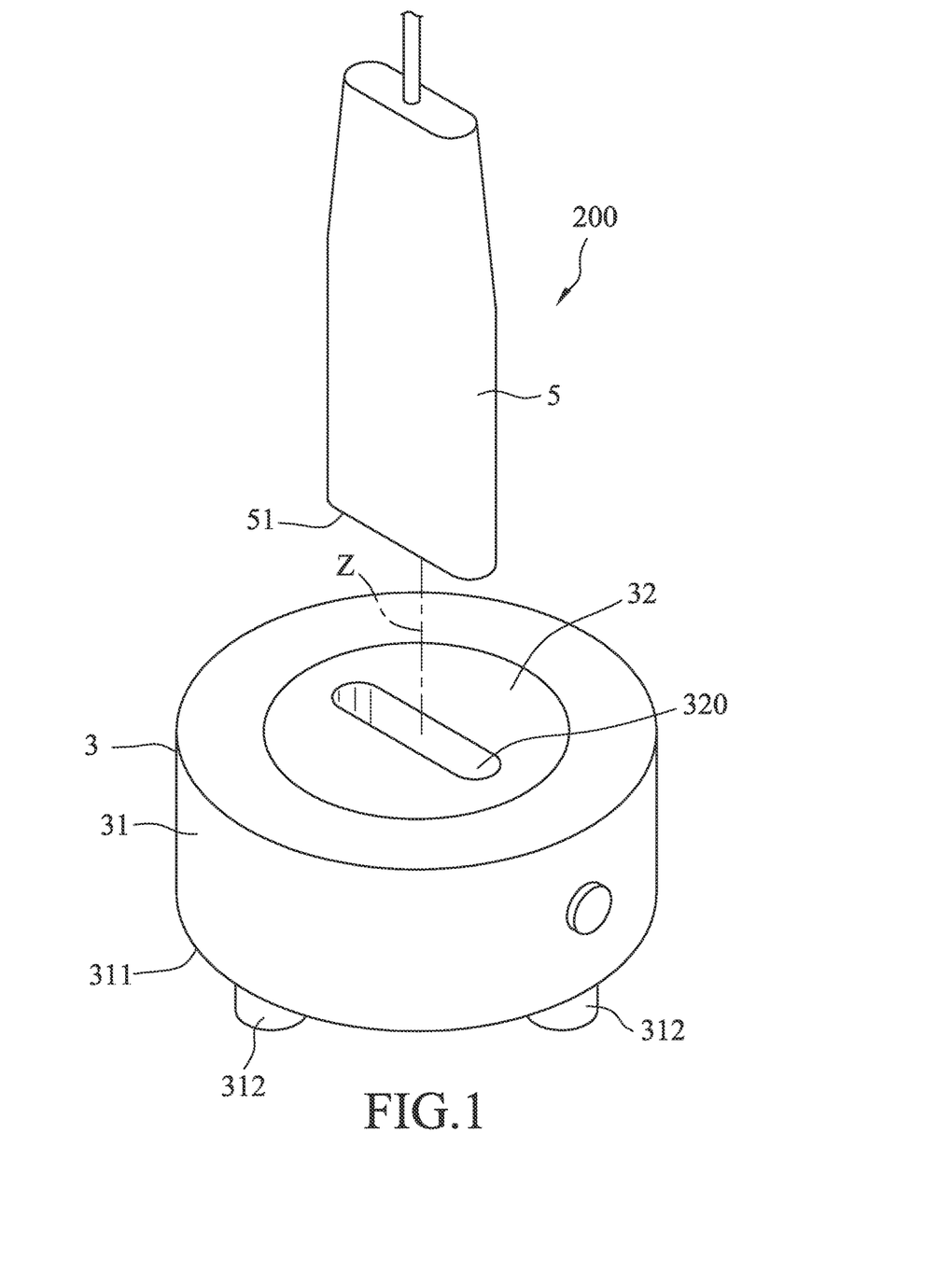
FIG. 1 is a perspective view illustrating an embodiment of an ultrasonic device according to the disclosure.
Figure 3:
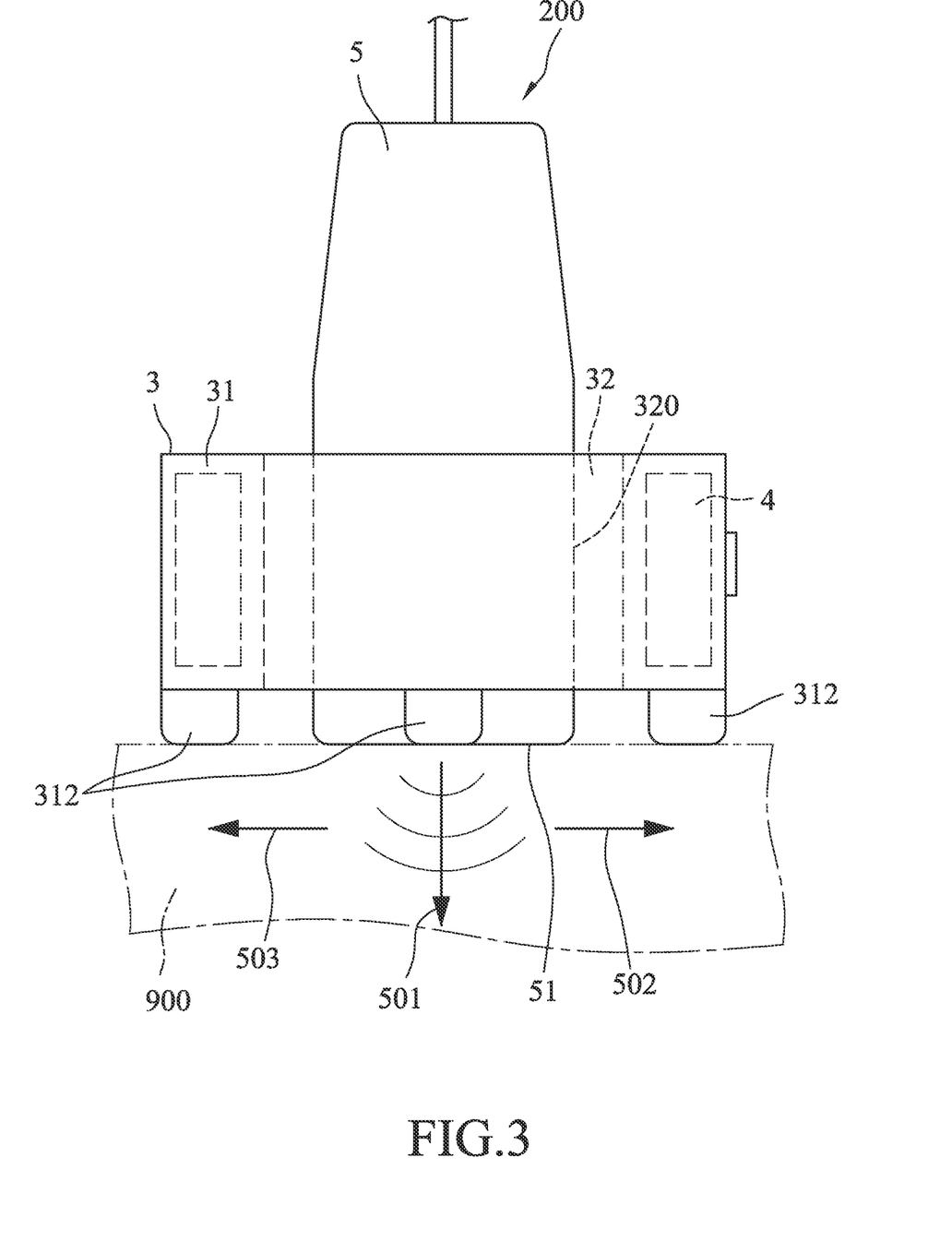
FIG. 3 is a side view of the embodiment.
Figure 4:
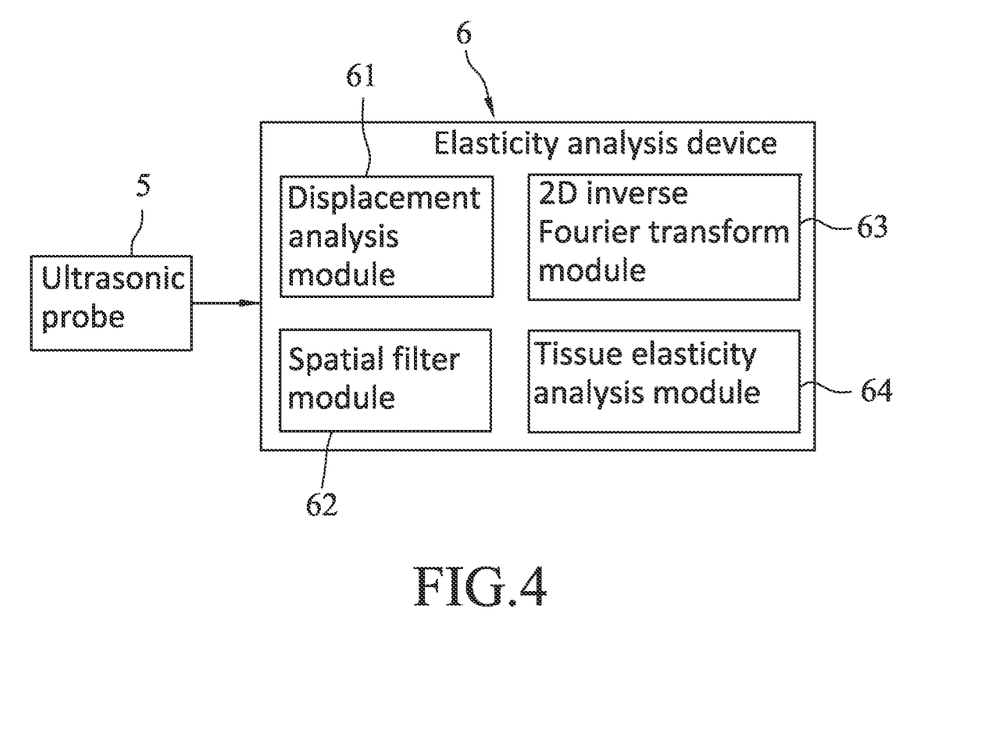
FIG. 4 is a block diagram illustrating the embodiment.

Referring to FIGS. 1, 3 and 4, an embodiment of a system for measuring elasticity of a biological issue 900 according to this disclosure is shown to include an ultrasonic device 200 and an elasticity analysis device 6. The ultrasonic device 200 is adapted for use on a surface of a biological tissue 900 (e.g., a body surface of a test subject), so as to acquire ultrasound images of the biological tissue. The elasticity analysis device 6 is communicatively connected to the ultrasonic device 200 for analyzing the ultrasound images acquired thereby, so as to obtain longitudinal elasticity data and lateral elasticity data of the biological tissue 900. In this embodiment, the elasticity analysis device 6 may be realized as a computer in which a computer program is installed, wherein the computer program is configured to include a displacement analysis module 61, a spatial filter module 62, a two-dimensional (2D) inverse Fourier transform module 63 and a tissue elasticity analysis module 64 that cooperatively calculate the longitudinal elasticity data and lateral elasticity data of the biological tissue 900 based on the ultrasound images acquired by the ultrasonic device 200.

In this embodiment, the ultrasonic device 200 is configured to emit an ultrasonic signal travelling as a fan-shaped arcing beam in a travelling direction defined as a longitudinal direction; a pair of opposite directions that are parallel to a chord length of the fan-shaped arcing beam are defined as lateral directions, which are perpendicular to the longitudinal direction. For ease of explanation, FIG. 2 defines an X-axis, a Y-axis and a Z-axis that intersect and that are perpendicular to each other, where the Z-axis extends along the longitudinal direction.

Figure 2:
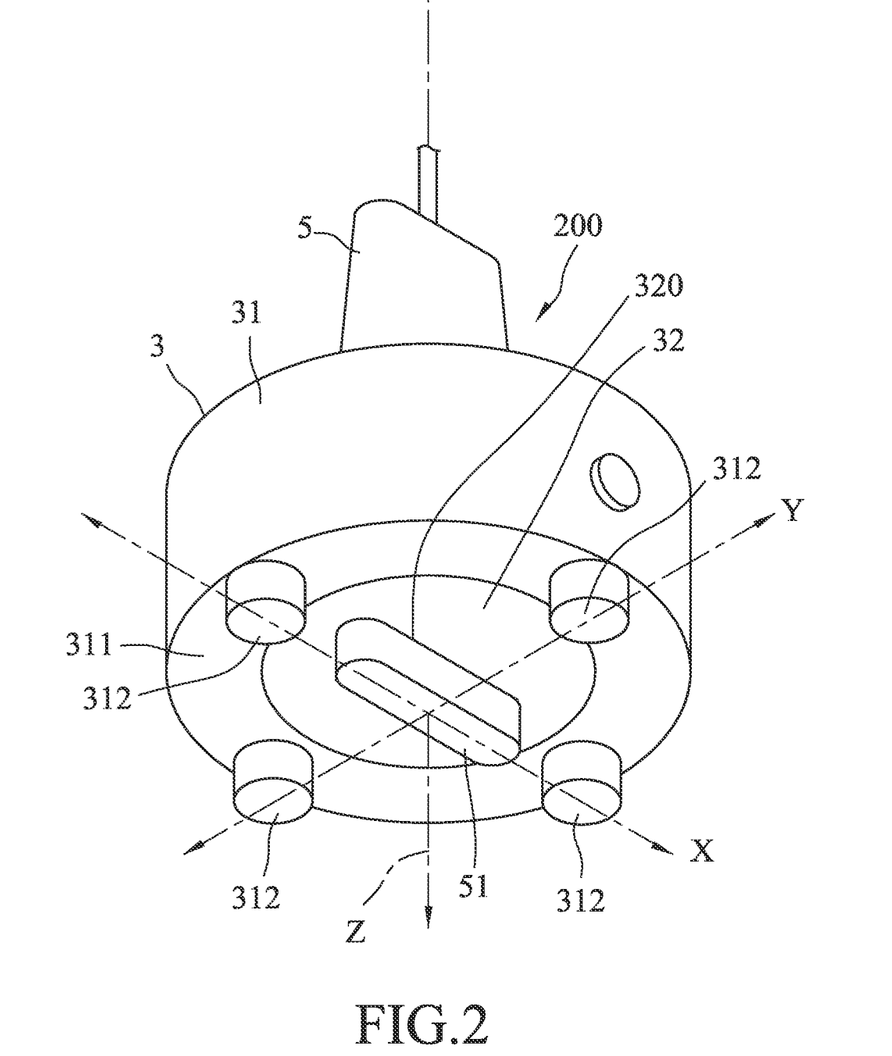
FIG. 2 is a perspective bottom view illustrating the embodiment.

Referring to FIGS. 1 to 3, the ultrasonic device 200 includes a base assembly 3, a vibrator 4 that is mounted to and disposed in the base assembly 3, and an ultrasonic probe 5 that is detachably inserted in the base assembly 3.

The base assembly 3 includes an annular base 31 that surrounds the Z-axis, and an installation base 32 that is coaxially disposed on the annular base 31.

The annular base 31 has an annular surface 311 that faces downwardly toward the biological tissue 900 and that surrounds the Z-axis, and at least two pairs of abutment protrusions 312 that protrude from the annular surface 311 for abutting against the biological tissue 900. For each pair of the abutment protrusions 312, the abutment protrusions 312 are disposed symmetrically with respect to the Z-axis. In this embodiment, the annular base 31 includes two pairs of the abutment protrusions 312; for one of these pairs (referred to as first pair of the abutment protrusions 312), the abutment protrusions 312 thereof are disposed on the X-axis and are symmetric with respect to the Z-axis, and for the other of these pairs (referred to as second pair of the abutment protrusions 312), the abutment protrusions 312 thereof are disposed on the Y-axis and are symmetric with respect to the Z-axis, but this disclosure is not limited to such. In other embodiments, the annular base 31 may include more than two pairs of the abutment protrusions 312, and the abutment protrusions 312 are, for example but not limited to, evenly distributed on the annular surface 311. The abutment protrusions 312 may be made of a material selected from a group consisting of ceramic materials, metals and hard polymers, and can be, for example but not limited to, steel, iron, hard plastic, etc.

Figure 6:
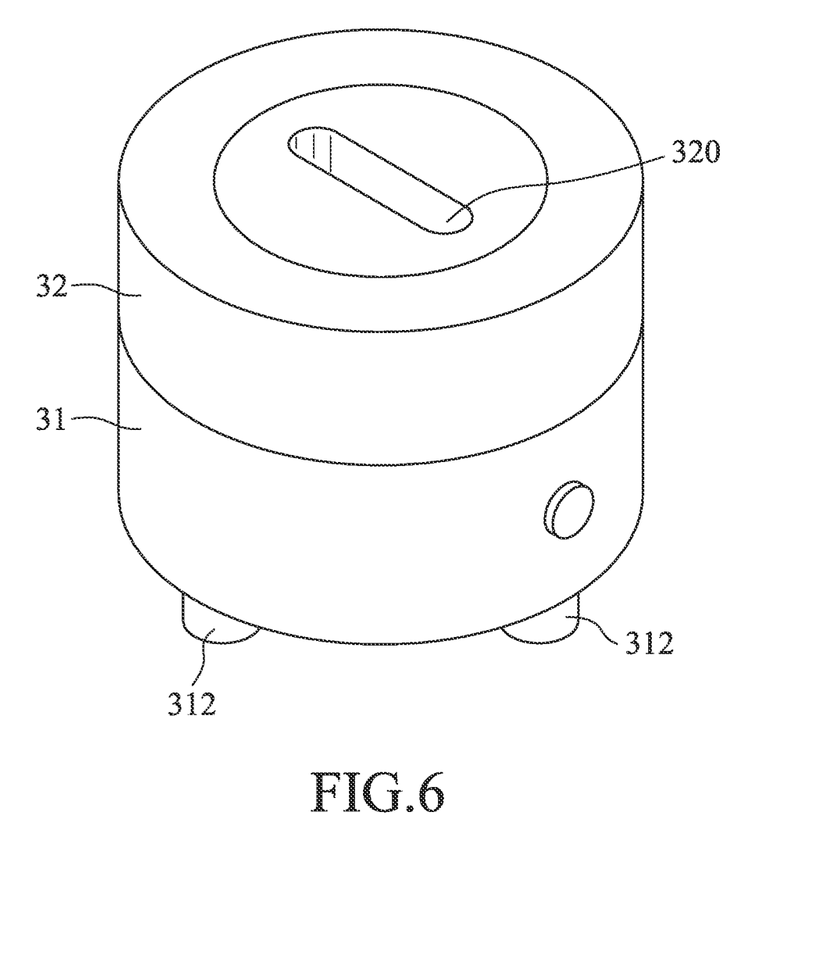
FIG. 6 is a perspective view illustrating a variation of the embodiment of the ultrasonic device.

In this embodiment, the installation base 32 is adapted to be disposed at an inner side of the annular base 31, is formed with an elongated installation through hole 320 that extends along the Z-axis, and is operable to rotate relative to the annular base 31 about the Z-axis between a first testing position and a second testing position that respectively correspond to the first and second pairs of the abutment protrusions 312. As an example, the annular base 31 may have a top opening that is slightly bigger than the installation base 32 so the installation base 32 can be placed in the annular base 31 from the top opening, and have a bottom opening that is smaller than the installation base 32 so the installation base 32 will not pass through the annular base 31 from the bottom opening while the installation through hole 320 is exposed from the bottom opening of the annular base 31. However, this disclosure is not limited to such a specific design. When the installation base 32 is positioned at the first testing position, a major axis of the installation through hole 320 extends through the first pair of the abutment protrusions 312 (i.e., extends along the X-axis). When the installation base 32 is positioned at the second testing position, the major axis of the installation through hole 320 extends through the second pair of the abutment protrusions 312 (i.e., extends along the Y-axis). In some embodiments that the annular base 31 includes more than two pairs of the abutment protrusions 312, the installation base 32 may be operable to rotate among more than two testing positions that respectively correspond to the pairs of the abutment protrusions 312. In practice, the installation base 32 is not limited to being disposed at an inner side of the annular base 31, and can be so disposed as long as the installation base 32 is operable to rotate relative to the annular base 31 about the Z-axis. For example, the installation base 32 may be disposed on top of the annular base 31 in some embodiments, as exemplarily illustrated in FIG. 6.

The vibrator 4 is mounted to the annular base 31, and is operable to vibrate, so as to induce vibration of the annular base 31 in the Z-axis, and thus apply mechanical waves to the biological tissue 900 through the abutment protrusions 312. The mechanical waves have a frequency in a range of from 100 Hz to 400 Hz. The mechanical waves may induce a longitudinal shear wave (referred to as longitudinal vibration shear wave) that travels in the longitudinal direction in the biological tissue 900. The mechanical waves applied through any one of the pairs of the abutment protrusions 312 may be coupled to each other to induce lateral shear waves (referred to as lateral vibration shear waves) that travel in opposite lateral directions parallel to a virtual line interconnecting the pair of the abutment protrusions 312. In some embodiments, the vibrator 4 may be mounted to the installation base 32, and this disclosure is not limited in this respect.

The ultrasonic probe 5 is detachably inserted in the installation through hole 320 along the Z-axis for abutting against the biological tissue 900 to perform ultrasonic testing on the biological tissue 900. In detail, the ultrasonic probe 5 has an ultrasonic measurement surface 51 to abut against the biological tissue 900, so as to perform image scanning on the biological tissue 900 through the ultrasonic measurement surface 51.

The ultrasonic probe 5 is operable to drive rotation of the installation base 32 relative to the annular base 31 about the Z-axis when inserted in the installation through hole 320, so as to switch the installation base 32 between the first testing position and the second testing position. When the installation base 32 is positioned in the first testing position or the second testing position, the ultrasonic probe 5 that is inserted in the installation through hole 32 is operable to produce an ultrasonic signal travelling as a fan-shaped arcing beam, of which a chord direction is parallel to the virtual line (i.e., the X-axis for the first testing position or the Y-axis for the second testing position in this embodiment) that interconnects the corresponding pair of the abutment protrusions 312. In other words, two ends of the fan-shaped arcing beam are aligned with the first pair of the abutment protrusions 312 when the installation base 32 is positioned in the first testing position, and are aligned with the second pair of the abutment protrusions 312 when the installation base 32 is positioned in the second testing position.

In this embodiment, when the installation base 32 is positioned in the first testing position or the second testing position, the ultrasonic probe 5 is operated to emit the ultrasonic signal to the biological tissue 900, which results in a shear wave (referred to as ultrasonic shear wave) travelling in the biological tissue 900, so as to perform image scanning on the biological tissue 900 to obtain first ultrasound images when the vibrator 4 does not vibrate, and to perform image scanning on the biological tissue 900 to consecutively obtain a plurality of second ultrasound images that serve as testing ultrasound images when the vibrator 4 is vibrating to apply the mechanical waves to the biological tissue 900.

The elasticity analysis device 6 is communicatively connected to the ultrasonic probe 5 for receiving and analyzing the first and second ultrasound images, so as to obtain longitudinal elasticity data and lateral elasticity data of the biological tissue 900.

In this embodiment, the displacement analysis module 61 is configured to perform averaging on the first ultrasound images, namely, to perform averaging on the pixels of the first ultrasound images at the same coordinates, so as to obtain a reference ultrasound image. The displacement analysis module 61 is further configured to convert each of the testing ultrasound images into a respective displacement image by first calculating, for each of pixels of the testing ultrasound image, a timewise displacement of the ultrasonic shear wave relative to the reference ultrasound image at a time point the testing ultrasound image was taken. In some embodiments, the timewise displacement of the ultrasonic shear wave relative to the reference ultrasound image can be calculated according to:

$$D_p = \frac{c}{4\pi f_c} \arctan\left( \frac{\sum_{m=0}^{M-1} Q(m,0) \sum_{m=0}^{M-1} I(m,i) - \sum_{m=0}^{M-1} I(m,0) \sum_{m=0}^{M-1} Q(m,i)}{\sum_{m=0}^{M-1} I(m,0) \sum_{m=0}^{M-1} I(m,i) - \sum_{m=0}^{M-1} Q(m,0) \sum_{m=0}^{M-1} Q(m,i)} \right),$$

where $D_p$ represents the timewise displacement, C represents a traveling speed of the ultrasonic shear wave in the biological tissue 900, which is usually about 1540 m/s, $f_c$ represents a center frequency of the ultrasonic shear wave, I(m,i) represents an in-phase signal acquired from the testing ultrasound image, I(m,0) represents an in-phase signal acquired from the reference ultrasound image, Q(m,i) represents a quadrature signal acquired from the testing ultrasound image, Q(m,0) represents an quadrature signal acquired from the reference ultrasound image, m represents an $m^{th}$ depth in the biological tissue 900 (an $m^{th}$ position in the longitudinal direction), and i represent an $i^{th}$ time point.

Since the frequency of motion noise resulting from displacement generated by breathing or other body activities is usually smaller than 20 Hz, and a displacement frequency of shear waves in soft tissues ranges between 100 Hz and 1500 Hz, the displacement analysis module 61 may further use a high-pass filter of 20 Hz and a low-pass filter of 1500 Hz to perform time-domain filtering on the timewise displacement of the ultrasonic shear wave for each of the testing ultrasound images so as to filter out the noises resulting from breathing and/or body activities.

Then, for each of the testing ultrasound images, the displacement analysis module 61 uses the timewise displacement of the ultrasonic shear wave thus filtered for the testing ultrasound image to compose the respective displacement image, so that the resultant displacement images respectively corresponding to the testing ultrasonic images correspond to different time points (i.e., the time points the testing ultrasound images were taken). For example, each pixel of each of the testing ultrasound images is converted into a value representing the timewise displacement of the ultrasonic shear wave at the pixel, so as to form a corresponding pixel in a corresponding displacement image.

In this embodiment, the displacement analysis module 61 uses autocorrelation to calculate, for each of the testing ultrasound images, a phase shift of the testing ultrasound image relative to the reference ultrasound image at a time point the testing ultrasound image was taken, so as to obtain the timewise displacement of the ultrasonic shear wave for each of the pixels of the testing ultrasound image. Using the autocorrelation to calculate the timewise displacement of the ultrasonic shear wave is commonly known in the art, so details thereof are omitted herein for the sake of brevity.

The spatial filter module 62 performs 2D Fourier transform on the displacement images that correspond to the different time points to transform the displacement images into a spatial frequency domain (SFD), such as the K-space, so as to obtain a plurality of SFD displacement images that respectively correspond to the displacement images. As an example, each of the SFD displacement images may be obtained according to:

$$F(k_x, k_y) = \sum_{m=0}^{M-1}\sum_{n=0}^{N-1} f(m,n) e^{-j2\pi\left(x\frac{m}{M}+y\frac{n}{N}\right)},$$

where $F(k_x, k_y)$ represents a result of the 2D Fourier transform (i.e., the SFD displacement image), $f(m,n)$ represents one of the displacement images, M and N respectively represent a number of pixels said one of the displacement images in the longitudinal direction and a number of pixels of said one of the displacement images in the lateral directions, and $k_x$ and $k_y$ respectively represent spatial frequencies after the 2D Fourier transform. For example, a positive $k_x$ represents an energy of the ultrasonic shear wave transmitted in a first lateral direction (e.g., a right direction), a negative $k_x$ represents the ultrasonic shear wave transmitted in a second lateral direction that is opposite to the first lateral direction (e.g., a left direction), a positive $k_y$ represents an energy of the ultrasonic shear wave transmitted in a first longitudinal direction (e.g., an upward direction), and a negative $k_y$ represents an energy of the ultrasonic shear wave transmitted in a second longitudinal direction that is opposite to the first longitudinal direction (e.g., a downward direction, which is the longitudinal direction in this embodiment).

Then, for each of the SFD displacement images, the spatial filter module 62 performs filtering on the SFD displacement image with respect to the longitudinal direction in which the ultrasonic signal travels to obtain a longitudinal SFD displacement image, and with respect to the lateral directions (i.e., the opposite chord directions of the ultrasonic signal that travels as the fan-shaped arcing beam) to obtain a set of lateral SFD displacement images that respectively correspond to the lateral directions. In this embodiment, the set of lateral SFD displacement images includes a first lateral SFD displacement image that corresponds to a first one of the lateral directions (referred to as first lateral direction) and a second lateral SFD displacement image that corresponds to a second one of the lateral directions (referred to as second lateral direction) opposite to the first lateral direction.

In this embodiment, for each of the SFD displacement images, the spatial filter module 62 uses a mask of a longitudinal 2D Fourier transform that corresponds to the longitudinal direction to perform filtering on the SFD displacement image to obtain the longitudinal SFD displacement image, uses a first mask of a lateral 2D Fourier transform that corresponds to the first lateral direction to perform filtering on the SFD displacement image to obtain the first lateral SFD displacement image, and uses a second mask of a lateral 2D Fourier transform that corresponds to the second lateral direction to perform filtering on the SFD displacement image to obtain the second lateral SFD displacement image.

As an example, the mask of the longitudinal 2D Fourier transform may be configured as a 2D matrix that is defined to be:

$$\begin{cases} \text{if } k_y > 0, m(k,l) = 1 \\ \text{else, } m(k,l) = 0 \end{cases},$$

and the first and second masks of the lateral 2D Fourier transform may be configured to respectively be 2D matrices of:

$$\begin{cases} \text{if } k_x > 0, m(k,l) = 1 \\ \text{else, } m(k,l) = 0 \end{cases}, \text{ and}$$

$$\begin{cases} \text{if } k_x < 0, m(k,l) = 1 \\ \text{else, } m(k,l) = 0 \end{cases},$$

where $m(k,l)$ represents an element of the matrix that corresponds to a pixel of the SFD displacement image at coordinates (k,l).

As illustrated in FIG. 3, an arrow 501 indicates the longitudinal direction, and arrows 502, 503 indicate the opposite lateral directions parallel to the virtual line interconnecting the abutment protrusions 312 that correspond to one of the testing positions in which the installation base 32 is currently positioned.

For each of the longitudinal SFD displacement images that are obtained respectively from the SFD displacement images and that respectively correspond to the different time points, the 2D inverse Fourier transform module 63 performs 2D inverse Fourier transform on the longitudinal SFD displacement image to transform the longitudinal SFD displacement image into the time domain, so as to obtain a longitudinal time-domain displacement image. As a result, a plurality of the longitudinal time-domain displacement images that respectively correspond to the longitudinal SFD displacement images and that respectively correspond to the different time points are obtained. For each of the sets of the lateral SFD displacement images that are obtained respectively from the SFD displacement images and that respectively correspond to the different time points, the 2D inverse Fourier transform module 63 performs the 2D inverse Fourier transform on the lateral SFD displacement images that correspond to opposite lateral directions to transform the set of the lateral SFD displacement images into the time domain, so as to obtain a set of lateral time-domain displacement images that respectively correspond to the opposite lateral directions. As a result, a plurality of sets of the lateral time-domain displacement images that respectively correspond to the sets of the lateral SFD displacement images and that respectively correspond to the different time points are obtained.

In the embodiment, the 2D inverse Fourier transform may be performed according to:

$$f(m,n) = \frac{1}{MN} \sum_{m=0}^{M-1}\sum_{n=0}^{N-1} F(k_x, k_y) e^{j2\pi\left(x\frac{m}{M}+y\frac{n}{N}\right)},$$

where $f(m,n)$ represents a signal in the time domain (e.g., each of the longitudinal time-domain displacement images or the lateral time-domain displacement images), $F(k_x, k_y)$ represents a signal in the spatial frequency domain (e.g., each of the longitudinal SFD displacement images or the lateral SFD displacement images), M and N respectively represent a number of pixels of said each of the longitudinal SFD displacement images or the lateral SFD displacement images) in the longitudinal direction and a number of pixels of said each of the longitudinal SFD displacement images or the lateral SFD displacement images) in the lateral directions, and $k_x$ and $k_y$ respectively represent the spatial frequencies.

The tissue elasticity analysis module 64 calculates longitudinal elasticity of the biological tissue 900 based on a timewise variation of phases of the longitudinal time-domain displacement images, and calculates lateral elasticities of the biological tissue 900 based on timewise variations of phases of the lateral time-domain displacement images.

In this embodiment, for each of multiple predetermined lateral positions on the biological tissue 900, the tissue elasticity analysis module 64 calculates a longitudinal wave speed data piece that is related to a wave speed of the longitudinal vibration shear wave with respect to the predetermined lateral position based on timewise variations of the phases of the longitudinal time-domain displacement images at different depths in the longitudinal direction from the predetermined lateral position. Then, the tissue elasticity analysis module 64 calculates the longitudinal elasticity of the biological tissue 900 based on the longitudinal wave speed data pieces calculated for the predetermined lateral positions on the biological tissue 900.

With respect to each of the lateral directions, for each of multiple predetermined depths in the biological tissue 900, the tissue elasticity analysis module 64 calculates a lateral wave speed data that is related to a wave speed of the lateral vibration shear wave with respect to the predetermined depth based on timewise variations of the phases of those of the lateral time-domain displacement images that correspond to the lateral direction at different positions in the lateral direction at the predetermined depth. Then, with respect to each of the lateral directions, the tissue elasticity analysis module 64 calculates the corresponding lateral elasticity of the biological tissue 900 based on the lateral wave speed data pieces calculated for the predetermined depths in the biological tissue 900 with respect to the lateral direction.

The longitudinal wave speed or the lateral wave speed may be calculated according to:

$$C_s = \frac{D}{T},$$

where $C_s$ represents a wave speed of the vibration shear wave, D represents a distance between two predetermined positions in the longitudinal direction or the lateral direction, and T represents a time difference of the vibration shear wave transmitted from one of the two predetermined positions to the other one of the two predetermined positions, which can be acquired from the corresponding longitudinal time-domain displacement images or the lateral time-domain displacement images.

The longitudinal elasticity and the lateral elasticities of the biological tissue may each be calculated according to:

$$E=3\rho c^2$$

where E represents the Young's modulus (i.e., the elasticity), $\rho$ represents the tissue density (which is usually set to 1080 kg/m$^3$), and C represents the wave speed.

The longitudinal elasticity and the lateral elasticities of the biological tissue 900 thus obtained can be used to indicate a quality of muscles or tendons, and thus can be used to make medical determinations related to muscles or tendons, such as making diagnosis on sarcopenia, evaluating an effect of rehabilitation, and so on.

Figure 5:
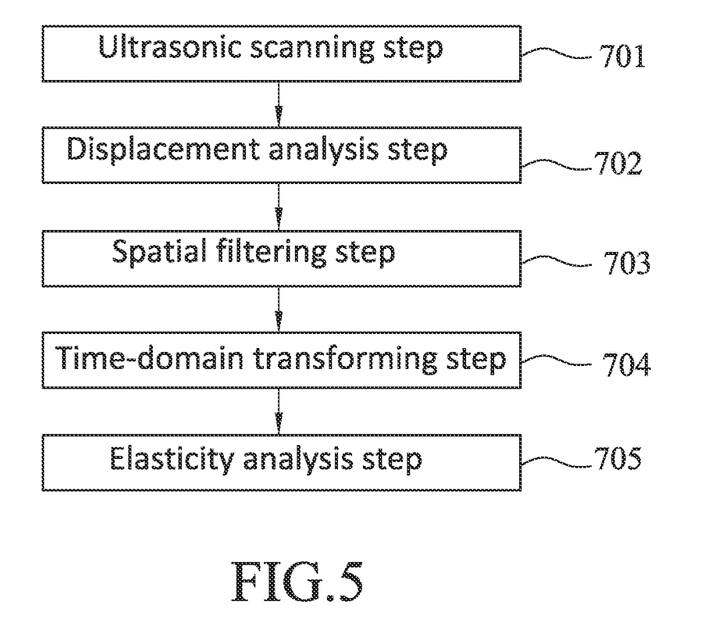
FIG. 5 is a flow chart illustrating steps of an embodiment of a method for using the embodiment of the ultrasonic device to measure elasticity of the biological tissue according to this disclosure.

Referring to FIGS. 3 to 5, an embodiment of a method for measuring elasticity of the biological tissue 900 according to this disclosure is shown to include steps 701-705.

In an ultrasonic scanning step 701, the installation base 32 is positioned in one of the testing positions, and the ultrasonic device 200 is placed on the biological tissue 900 with the abutment protrusions 312 abutting against a surface of the biological issue 900. The ultrasonic probe 5 is inserted in the installation through hole 320 to have the ultrasonic measurement surface 51 abut against the biological tissue 900. Then, the ultrasonic probe 5 is operated to perform continuous image scanning on the biological tissue 900 when the vibrator 4 does not vibrate, so as to obtain the first ultrasound images. A number of the first ultrasound images obtained may be, for example but not limited to, ten. Subsequently, the ultrasonic probe 5 is operated to perform, when the vibrator 4 is operated to be vibrating to apply a mechanical wave to the biological tissue 900, continuous image scanning on the biological tissue 900 with a predetermined scanning frequency (e.g., 5 MHz), so as to obtain the second ultrasound images (i.e., the testing ultrasound images). A number of the testing ultrasound images obtained may be, for example but not limited to, one hundred.

In a displacement analysis step 702, the elasticity analysis device 6 performs averaging on the first ultrasound images to obtain the reference ultrasound image, and calculates, for each of the testing ultrasound images, the timewise displacement of the ultrasonic shear wave relative to the reference ultrasound image at a time point the testing ultrasound image was taken, uses the high-pass filter of 20 Hz and the low-pass filter of 1500 Hz to perform time-domain filtering on the timewise displacement of the ultrasonic shear wave, and uses the timewise displacement of the ultrasonic shear wave thus filtered to compose the displacement image corresponding to the testing ultrasound image. As a result, a plurality of the displacement images that respectively correspond to the testing ultrasound images and that respectively correspond to different time points at which the testing ultrasound images were taken are obtained.

In a spatial filtering step 703, the elasticity analysis device 6 performs 2D Fourier transform on the displacement images, so as to transform the displacement images into the SFD displacement images that respectively correspond to the displacement images (SPD transforming step). Then, the elasticity analysis device 6 uses the mask of the longitudinal 2D Fourier transform to perform filtering on the SFD displacement images to obtain the longitudinal SFD displacement images, uses the first mask and the second mask of the lateral 2D Fourier transform to perform filtering on the SFD displacement images to obtain the sets of the lateral SFD displacement images. The lateral SFD displacement images in each set respectively correspond to the opposite lateral directions.

In a time-domain transforming step 704, the elasticity analysis device 6 performs 2D inverse Fourier transform on the longitudinal SFD displacement images to obtain the longitudinal time-domain displacement images, and performs 2D inverse Fourier transform on the sets of the lateral SFD displacement images to obtain the sets of the lateral time-domain displacement images. The longitudinal time-domain displacement images respectively correspond to the longitudinal SFD displacement images and respectively correspond to the different time points. The sets of the lateral time-domain displacement images respectively correspond to the sets of the lateral SFD displacement images, and respectively correspond to the different time points.

In the elasticity analysis step 705, for each of the predetermined lateral positions on the biological tissue 900, the elasticity analysis device 6 calculates the longitudinal wave speed data piece based on timewise variations of the phases of the longitudinal time-domain displacement images at different depths in the longitudinal direction from the predetermined lateral position, and the elasticity analysis device 6 then calculates the longitudinal elasticity of the biological tissue 900 based on the longitudinal wave speed data pieces calculated for the predetermined lateral positions on the biological tissue 900.

Similarly, with respect to each of the lateral directions, for each of multiple predetermined depths in the biological tissue 900, the tissue elasticity analysis device 6 calculates a lateral wave speed data based on timewise variations of the phases of those of the lateral time-domain displacement images that correspond to the lateral direction at different positions in the lateral direction at the predetermined depth, and the tissue elasticity analysis device 6 then calculates, for each of the lateral directions, the lateral elasticity of the biological tissue 900 that corresponds to the lateral direction based on the lateral wave speed data pieces calculated for the predetermined depths in the biological tissue 900 with respect to the lateral direction.

In summary, by virtue of using a pair of the abutment protrusions 312 to apply mechanical waves to the biological tissue 900, tissue elasticities with respect to the longitudinal direction and two opposite lateral directions can be measured at the same time. That is, a single measurement can obtain elasticities of the biological tissue 900 with respect to three directions.

In addition, by virtue of the installation base 32 that is coaxially disposed on and rotatable relative to the annular base 31 about the Z-axis, the ultrasonic device 200 can perform elasticity measurement for different longitudinal sections from a single site of the biological tissue 900 without the position of the ultrasonic device 200 being changed.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. An ultrasonic device for use on a biological tissue, comprising:
    a base assembly including:
        an annular base that surrounds an Z-axis, and that has an annular surface disposed to face the biological tissue and surrounding the Z-axis, and at least two pairs of abutment protrusions that protrude from said annular surface for abutting against the biological tissue, wherein, for each pair of said abutment protrusions, said abutment protrusions are disposed symmetrically with respect to the Z-axis; and
        an installation base that is coaxially disposed on said annular base and that is operable to rotate relative to said annular base about the Z-axis between at least two testing positions that respectively correspond to said at least two pairs of said abutment protrusions, said installation base being formed with an installation through hole that extends along the Z-axis;
    a vibrator that is mounted to said base assembly, and that is operable to vibrate for applying a mechanical wave to the biological tissue through said abutment protrusions, the mechanical wave having a frequency in a range of from 100 Hz to 400 Hz; and
    an ultrasonic probe inserted into said installation through hole along the Z-axis for abutting against the biological tissue to perform ultrasonic testing on the biological tissue;
    wherein, when said installation base is positioned in any one of said at least two testing positions, said ultrasonic probe that is inserted in said installation through hole is operable to produce an ultrasonic signal travelling as a fan-shaped arcing beam, of which a chord direction is parallel to a virtual line that interconnects the corresponding one of said at least two pairs of said abutment protrusions.

2. The ultrasonic device of claim 1, wherein said abutment protrusions are made of a material selected from a group consisting of ceramic materials, metals and polymers.

3. A method for measuring elasticity of a biological tissue, comprising:
    a first scanning step of using the ultrasonic device of claim 1 to perform, when the installation base is positioned in one of the at least two testing positions, image scanning on the biological tissue when the vibrator does not vibrate to obtain a reference ultrasound image, wherein the ultrasonic signal induces an ultrasonic shear wave that travels in the biological issue;
    a second scanning step of using the ultrasonic probe to perform, when the installation base is positioned in said one of the at least two testing positions and the vibrator is vibrating to apply a mechanical wave to the biological tissue, image scanning on the biological tissue with a predetermined scanning frequency, so as to obtain a plurality of testing ultrasound images;
    a displacement analysis step of calculating, for each of the testing ultrasound images, a timewise displacement of the ultrasonic shear wave relative to the reference ultrasound image at a time point the testing ultrasound image was taken, so as to convert the testing ultrasound image into a respective displacement image;
    a spatial-frequency-domain (SFD) transforming step of transforming the displacement images that correspond to the testing ultrasound images into a spatial frequency domain, so as to obtain a plurality of SFD displacement images that respectively correspond to the displacement images;

a first filtering step of performing, for each of the SFD displacement images, filtering on the SFD displacement image with respect to a longitudinal direction in which the ultrasonic signal travels to obtain a longitudinal SFD displacement image, the longitudinal direction being parallel to the Z-axis;

a second filtering step of performing, for each of the SFD displacement images, filtering on the SFD displacement image with respect to lateral directions that are perpendicular to the longitudinal direction to obtain a set of lateral SFD displacement images that respectively correspond to the lateral directions;

a first time-domain transforming step of transforming the longitudinal SFD displacement images that are obtained respectively from the SFD displacement images into a time domain, so as to obtain a plurality of longitudinal time-domain displacement images;

a second time-domain transforming step of transforming the sets of the lateral SFD displacement images that are obtained respectively from the SFD displacement images into the time domain, so as to obtain a plurality of sets of lateral time-domain displacement images, wherein the lateral time-domain displacement images in each of the sets respectively correspond to the lateral directions; and an elasticity analysis step of calculating longitudinal elasticity of the biological tissue based on a timewise variation of phases of the longitudinal time-domain displacement images, and calculating lateral elasticities of the biological tissue based on timewise variations of phases of the lateral time-domain displacement images;

wherein the longitudinal elasticity and the lateral elasticities of the biological tissue are usable for making medical determinations related to muscles or tendons.

4. The method of claim 3, wherein the second filtering step includes, for each of the SFD displacement images, using a mask of a lateral two-dimensional (2D) Fourier transform that corresponds to one of the lateral directions to perform filtering on the SFD displacement image to obtain one of the lateral SFD displacement images that corresponds to said one of the lateral directions in the set;

wherein the second time-domain step includes performing, for each of the sets of the lateral SFD displacement images, 2D inverse Fourier transform on said one of the lateral SFD displacement images to obtain one of the lateral time-domain displacement images that corresponds to said one of the lateral directions;

wherein the elasticity analysis step includes calculating, based on a timewise variation of phases of those of the lateral time-domain displacement images that correspond to said one of the lateral directions, a lateral elasticity data piece that corresponds to said one of the lateral directions.

5. The method of claim 3, wherein the lateral directions include a first lateral direction and a second lateral direction opposite to each other and parallel to the virtual line, which interconnects one of said at least two pairs of the abutment protrusions that corresponds to said one of the at least two testing positions;

wherein each of the sets of the lateral SFD displacement images includes a first lateral SFD displacement image and a second lateral SFD displacement image that respectively correspond to the first lateral direction and the second lateral direction;

wherein each of the sets of the lateral time-domain displacement images includes a first lateral time-domain displacement image and a second lateral time-domain displacement image that respectively correspond to the first lateral direction and the second lateral direction;

wherein the second filtering step includes, for each of the SFD displacement images, using a first mask and a second mask of a lateral two-dimensional (2D) Fourier transform that respectively correspond to the first lateral direction and the second lateral direction to perform filtering on the SFD displacement image to respectively obtain the first lateral SFD displacement image and the second lateral SFD displacement image of the set of the lateral SFD displacement images that corresponds to the SFD displacement image;

wherein the second time-domain transforming step includes performing, for each of the sets of the lateral SFD displacement images, 2D inverse Fourier transform on the first lateral SFD displacement image and the second lateral SFD displacement image to obtain the first lateral time-domain displacement image and the second lateral time-domain displacement image that corresponds to the first lateral direction and the second lateral direction, respectively;

wherein the elasticity analysis step includes calculating, based on a timewise variation of phases of the first lateral time-domain displacement images in the sets of the lateral time-domain displacement images in the first lateral direction, a first lateral elasticity data piece that corresponds to the first lateral direction, and calculating, based on a timewise variation of phases of the second lateral time-domain displacement images in the sets of the lateral time-domain displacement images in the second lateral direction, a second lateral elasticity data piece that corresponds to the second lateral direction.

6. The method of claim 3, wherein the elasticity analysis step includes:

calculating, for each of multiple predetermined lateral positions on the biological tissue, a longitudinal wave speed data piece that is related to a wave speed of a longitudinal vibration shear wave with respect to the predetermined lateral position based on timewise variations of the phases of the longitudinal time-domain displacement images at different depths in the longitudinal direction from the predetermined lateral position; and calculating the longitudinal elasticity of the biological tissue based on the longitudinal wave speed data pieces calculated for the predetermined lateral positions on the biological tissue.

7. The method of claim 3, wherein the elasticity analysis step includes:

with respect to each of the lateral directions, calculating, for each of multiple predetermined depths in the biological tissue, a lateral wave speed data that is related to a wave speed of a lateral vibration shear wave with respect to the predetermined depth based on timewise variations of the phases of those of the lateral time-domain displacement images that correspond to the lateral direction at different positions in the lateral direction at the predetermined depth; and with respect to each of the lateral directions, calculating a corresponding one of the lateral elasticities of the biological tissue based on the lateral wave speed data pieces calculated for the predetermined depths in the biological tissue with respect to the lateral direction.

8. The method of claim 3, wherein the displacement analysis step includes:
- using a high-pass filter of 20 Hz and a low-pass filter of 1500 Hz to perform time-domain filtering on the timewise displacement of the ultrasonic shear wave for each of the testing ultrasound images; and
- for each of the testing ultrasound images, using the timewise displacement of the ultrasonic shear wave thus filtered for the testing ultrasound image to compose the respective displacement image.

* * * * *